United States Patent
Hargreaves

(10) Patent No.: US 6,919,181 B2
(45) Date of Patent: Jul. 19, 2005

(54) METHODS FOR GENERATING LIGAND ARRAYS

(75) Inventor: John S. Hargreaves, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 113 days.

(21) Appl. No.: 10/106,685

(22) Filed: Mar. 25, 2002

(65) Prior Publication Data

US 2003/0180732 A1 Sep. 25, 2003

(51) Int. Cl.[7] .............................. C12Q 1/68; C12M 1/36; C07H 21/04
(52) U.S. Cl. ............................ 435/6; 435/7.1; 435/174; 435/283.1; 435/287.2; 536/23.1; 536/25.3
(58) Field of Search ............................ 435/6, 7.1, 174, 435/283.1; 438/283.1, 287.2; 536/23.1, 25.3

(56) References Cited

U.S. PATENT DOCUMENTS

| | | | |
|---|---|---|---|
| 6,258,454 B1 | | 7/2001 | Lefkowitz et al. |
| 6,319,674 B1 | | 11/2001 | Fulcrand et al. |
| 6,362,183 B1 | * | 3/2002 | Freskos et al. .......... 514/238.2 |
| 6,410,675 B2 | * | 6/2002 | McGall et al. ................ 528/10 |
| 6,677,163 B1 | * | 1/2004 | Boukherroub et al. ...... 436/527 |
| 2002/0004535 A1 | * | 1/2002 | Kotsuka et al. ............... 521/53 |

OTHER PUBLICATIONS

Rousch et al "STudies on the synthesis of aureolic acid antibioorics" J Amer. Chem. Soc. 1995, 117: 2236–2250.*
Kunesch et al Tetrahedron Letters, 1987, 28: 3569–3572.*
Plattner et al "Synthesis of some DE and DCE ring analogs of camptothecin" J. Amer. Chem. Soc. 1972, 94: 8613–8615.*
M. Pomerantz et al. "Coverage of Si Substrates by Self-Assembling Monolayers and Multilayers as Measured by IR, Wettability and X–Ray Diffraction" Thin Solid Films, 132 (1985) 153–162.
A.B. Sieval et al. "Highly Stable Si–C Linked Functionalized Monolayers on the Silicon (100) Surface" Langmuir 1998, 14, 1759–1768.

* cited by examiner

Primary Examiner—B J Forman

(57) ABSTRACT

Methods of producing ligand arrays, e.g., polypeptide and nucleic acid arrays, as well as the arrays produced thereby, methods for use of the arrays and kits that include the same, are provided. In the subject methods, a substrate having a surface displaying carboxylic ester functional groups that produce surface bound hydroxyl functional groups upon hydrolysis is first provided. Next, the functional groups are hydrolyzed to hydroxyl functional groups. The resultant substrate, optionally after an additional functionalization step, is then contacted with ligands, e.g., via deposition of each different ligand onto a different region of the surface, resulting in covalent attachment of the contacted ligands to the surface.

23 Claims, No Drawings

METHODS FOR GENERATING LIGAND ARRAYS

TECHNICAL FIELD

The field of this invention is ligand arrays, including protein and nucleic acid arrays.

BACKGROUND OF THE INVENTION

Arrays of binding agents (ligands), such as nucleic acids and polypeptides, have become an increasingly important tool in the biotechnology industry and related fields. These binding agent or ligand arrays, in which a plurality of binding agents are positioned on a solid support surface in the form of an array or pattern, find use in a variety of applications, including gene expression analysis, drug screening, nucleic acid sequencing, mutation analysis, and the like.

A feature of many arrays that have been developed is that each of the polymeric compounds of the array is stably attached to a discrete location on the array surface, such that its position remains constant and known throughout the use of the array. Stable attachment is achieved in a number of different ways, including covalent bonding of the polymer to the support surface and non-covalent interaction of the polymer with the surface.

Where the ligands of the arrays are polymeric, e.g., as is the case with nucleic acid and polypeptide arrays, there are two main ways of producing such arrays, i.e., via in situ synthesis in which the polymeric ligand is grown on the surface of the substrate in a step-wise fashion and via deposition of the full ligand, e.g., a presynthesized nucleic acid/polypeptide, cDNA fragment, etc., onto the surface of the array. In many situations where the desired polymeric ligands are long, the latter protocol of depositing full ligands on the substrate surface is desirable.

A number of different protocols have been developed in which full ligands are deposited onto the surface of an array, where such methods include those in which polylysine is adsorbed onto the surface of a glass support, those in which the surface of a glass support is modified via silylation to display various functional groups, and the like.

However, there is continued interest in the development of new protocols for producing arrays via deposition of full ligands onto the surface of the array. Of particular interest would be the development of protocols that provide for covalent attachment of full ligands, e.g., presynthesized nucleic acids, cDNAs and the like, following deposition of the full ligands on the support surface.

Relevant Literature

U.S. patents of interest include: U.S. Pat. Nos. 6,319,674 and 6,258,454; as well as the references cited therein. Also of interest are Pomerantz et al., Thin Solid Films (1985) 132: 153–162; and Sudholter et al, Langmuir (1998) 14: 1759 to 1768.

SUMMARY OF THE INVENTION

Methods of producing ligand arrays, e.g., polypeptide and nucleic acid arrays, as well as the arrays produced thereby, methods for use of the arrays and kits that include the same, are provided. In the subject methods, a substrate having surface displaying hydrolyzable functional groups, e.g., acid or alkali hydrolyzable functional groups, that produce hydroxyl functional groups upon hydrolysis is first provided. Next, the hydrolyzable functional groups are converted to hydroxyl functional groups. The resultant substrate, optionally after an additional functionalization step, is then contacted with ligands, e.g., via deposition of each different ligand onto a different region of the surface, resulting in covalent attachment of the contacted ligands to the surface.

Definitions

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any polymer compound produced by amide formation between a α-carboxyl group of one amino acid and an α-amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g. deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The term "functionalization" as used herein relates to modification of a solid substrate to provide a plurality of functional groups on the substrate surface. By a "functionalized surface" as used herein is meant a substrate surface that has been modified so that a plurality of functional groups are present thereon.

The terms "reactive site" or "reactive group" refer to moieties that can be used as the starting point in a synthetic organic process. This is contrasted to "inert" hydrophilic groups that could also be present on a substrate surface, e.g., hydrophilic sites associated with polyethylene glycol, a polyamide or the like.

The "surface energy" $\gamma$ (measured in ergs/cm$^2$) of a liquid or solid substance pertains to the free energy of a molecule on the surface of the substance, which is necessarily higher than the free energy of a molecule contained in the interior of the substance; surface molecules have an energy roughly 25% above that of interior molecules. The term "surface tension" refers to the tensile force tending to draw surface molecules together, and although measured in different units (as the rate of increase of surface energy with area, in dynes/cm), is numerically equivalent to the corresponding surface energy. By modifying a substrate surface to "reduce" surface energy is meant lowering the surface energy below that of the unmodified surface.

The term "monomer" as used herein refers to a chemical entity that can be covalently linked to one or more other such entities to form an polymer. Examples of "monomers" include nucleotides, amino acids, saccharides, peptoids, other reactive organic molecules and the like. In general, the monomers used in conjunction with the present invention have first and second sites (e.g., C-termini and N-termini(for proteins), or 5' and 3' sites(for oligomers, RNA's, cDNA's, and DNA's)) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide base, etc.). In the art synthesis of biomolecules of this type utilize an initial substrate-bound monomer that is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2–50 monomers, preferably about 2–20, more preferably about 3–10 monomers.

The term "ligand" as used herein refers to a moiety that is capable of covalently or otherwise chemically binding a compound of interest. The arrays of solid-supported ligands produced by the subject methods can be used in screening or separation processes, or the like, to bind a component of interest in a sample. The term "ligand" in the context of the invention may or may not be an "oligomer" as defined above. However, the term "ligand" as used herein may also refer to a compound that is "pre-synthesized" or obtained commercially, and then attached to the substrate.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, $\alpha$-aminoisobutyric acid, sarcosine, citrulline, cysteic acid, t-butylglycine, t-butylalanine, phenylglycine, cyclohexylalanine, $\beta$-alanine, 4-aminobutyric acid, and the like.

The terms "protection and "deprotection" as used herein relate, respectively, to the addition and removal of chemical protecting groups using conventional materials and techniques within the skill of the art and/or described in the pertinent literature; for example, reference may be had to Greene et al., *Protective Groups in Organic Synthesis*, 2nd Ed., New York: John Wiley & Sons, 1991. Protecting groups prevent the site to which they are attached from participating in the chemical reaction to be carried out.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkoxy" as used herein refers to a substituent —O—R wherein R is alkyl as defined above. The term "lower alkoxy" refers to such a group wherein R is lower alkyl.

The term "alkylene" as used herein refers to a difunctional saturated branched or unbranched hydrocarbon chain containing from 1 to 24 carbon atoms, and includes, for example, methylene (—$CH_2$—), ethylene (—CH2—$CH_2$—), propylene (—CH2—$CH_2$—$CH_2$—), 2-methylpropylene (—CH2—CH($CH_3$)—$CH_2$—), hexylene (—$(CH_2)_6$—), and the like. "Lower alkylene" refers to an alkylene group of 1 to 6, more preferably 1 to 4, carbon atoms.

The terms "halogen" or "halo" are used in the conventional sense to refer to a chloro, bromo, fluoro or iodo substituent.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

"Hydrolysis" means reaction with water, or the ions of water, where the reaction results in a bond cleavage. In many embodiments of the subject invention, a carboxylic ester is subjected to a hydrolysis, i.e., is hydrolyzed, to produce a carboxylic acid and a hydroxy group.

DESCRIPTION OF THE SPECIFIC EMBODIMENTS

Methods of producing ligand arrays, e.g., polypeptide and nucleic acid arrays, as well as the arrays produced thereby, methods for use of the arrays and kits that include the same, are provided. In the subject methods, a substrate having a surface displaying hydrolyzable functional groups (e.g., carboxylic ester functional groups) that produce surface bound hydroxyl functional groups upon hydrolysis is first provided. Next, the hydrolyzable functional groups are converted to hydroxyl functional groups. The resultant substrate, optionally after an additional functionalization step, is then contacted with ligands, e.g., via deposition of each different ligand onto a different region of the surface, resulting in covalent attachment of the contacted ligands to the surface.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components which are described in the publications which might be used in connection with the presently described invention.

As summarized above, the subject invention provides methods of producing ligand arrays. In further describing the subject invention, the subject methods are described first in greater detail, followed by a more in-depth review of the arrays produced by the subject methods, representative applications in which the arrays find use, and kits for use in practicing the subject methods.

Methods

As summarized above, the subject invention provides methods of producing ligand arrays. In the subject methods, the first step is to provide a substrate having a surface that displays hydrolyzable groups (e.g., acid or alkali hydrolyzable functional groups, which produce hydroxyl functional groups upon hydrolysis, e.g., upon exposure to either acid or alkali hydrolysis conditions. Next, the hydrolyzable groups are converted to hydroxyl functional groups, e.g., by acid or alkali hydrolysis. Following this conversion step, (and optionally a further functionalization step) the substrate surface is contacted with ligands resulting in covalent linkage of the ligands to the surface so as to produce a ligand array. Each of these steps is now described in greater detail below.

Providing a Substrate Having a Surface Displaying Hydrolyzable Functional Groups The first step in the subject methods is to provide a substrate having a surface which displays hydrolyzable functional groups that produce hydroxyl functional groups upon hydrolysis. The groups may be acid or alkali hydrolyzable groups, which produce the desired hydroxyl functional groups upon exposure to either acid or alkali hydrolysis conditions, respectively. Such a substrate may be provided using any convenient protocol. One way to provide such a substrate is to employ the following protocol.

In this protocol, the surface of a solid substrate is first contacted with a derivatizing composition that contains one or more types of silanes, where in many but not all embodiments the composition contains a mixture of silanes, under reaction conditions effective to couple the silanes to the substrate surface via reactive hydrophilic moieties present on the substrate surface. The reactive hydrophilic moieties on the substrate surface are typically hydroxyl groups, carboxyl groups, aldehyde, thiol groups, and/or substituted or unsubstituted amino groups, although, preferably, the reactive hydrophilic moieties are hydroxyl groups. The substrate may comprise any material that has a plurality of reactive hydrophilic sites on its surface, or that can be treated or coated so as to have a plurality of such sites on its surface. Suitable materials include, but are not limited to, supports that are typically used for solid phase chemical synthesis, e.g., cross-linked polymeric materials (e.g., divinylbenzene styrene-based polymers), agarose (e.g. SEPHAROSE™), dextran (e.g., SEPHADEX™), cellulosic polymers, polyacrylamides, silica, glass (particularly controlled pore glass, or "CPG") ceramics, and the like. The supports may be obtained commercially and used as is, or they may be treated or coated prior to functionalization. The substrate is typically flat with the contacted surface being planar (although these are not requirements).

The derivatizing composition contains at least one type of silane, where the silane includes a hydrolyzable functional group, e.g., acid or alkali hydrolyzable functional group, that produces a hydroxyl functional upon exposure to hydrolysis conditions, e.g., either acid or alkali hydrolysis conditions, as described in greater detail below. In many embodiments, the derivatizing composition may include two types of silanes, a first silane that may be represented as $R^2$-Si $(R^L R^x R^y)$ and second silane having the formula $R^2$-$(L)_n$-Si $(R^L R^x R^y)$. In these formulae, the $R^L$, which may be the same or different, are leaving groups, the $R^x$ and $R^y$, which may be the same or different, are either lower alkyl or leaving groups like $R^L$, $R^1$ is a chemically inert moiety that upon binding to the substrate surface lowers the surface energy thereof, n is 0 or 1, L is a linking group, and $R^2$ is the hydrolyzable functional group as summarized above and described in greater detail below. In those embodiments where the surface is contacted with only a single type of silane, the silane is the $R^2$ containing silane described above. Reaction of the substrate surface with the derivatizing composition is carried out under reaction conditions effective to couple the silane(s) to the surface hydrophilic moieties and thereby provide —Si—$R^1$ groups and —Si-$(L)_n$-$R^2$ groups on the substrate surface.

More specifically, the $R^L$ moieties, which are leaving groups, are such that they enable binding of the silanes to the surface. Typically, the leaving groups are hydrolyzable so as to form a silanol linkage to surface hydroxyl groups. Examples of suitable leaving groups include, but are not limited to, halogen atoms, particularly chloro, and alkoxy moieties, particularly lower alkoxy moieties. The $R^x$ and $R^y$ are either lower alkyl, e.g., methyl, ethyl, isopropyl, n-propyl, t-butyl, or the like, or leaving groups as just described with respect to $R^L$. Thus, each type of silane will generally contain a trichlorosilyl functionality, a tri(lower) alkoxysilyl functionality such as trimethoxysilyl, mixed functionalities such as diisopropylchlorosilyl, dimethylchlorosilyl, ethyldichlorosilyl, methylethylchlorosilyl or the like.

In those embodiments where a mixture of silanes make up the derivatizing composition, the first silane is a derivatizing agent that reduces surface energy as desired, while the second silane provides the hydrolyzable functionality. Thus, with respect to the first silane, coupling to the substrate yields surface —Si—$R^1$ groups as explained above, wherein $R^1$ is a chemically inert moiety that upon binding to the substrate surface lowers surface energy. By "chemically inert" is meant that $R^1$ will not be cleaved or modified when the functionalized substrate is used for its intended purpose, e.g., in solid phase chemical synthesis, hybridization assays, or the like. Typically, $R^1$ is an alkyl group, generally although not necessarily containing in the range of 2 to 24 carbon atoms, preferably in the range of 10 to 18 carbon atoms.

The second silane, upon coupling, provides surface —Si-$(L)_n$-$R^2$ groups, where $R^2$ is the hydrolyzable functionality. Of course, if the $R^x$ and $R^y$ are not leaving groups, the surface moieties provided will actually be —Si$R^x R^y$-$(L)_n$-$R^2$ groups, which applicants intend to encompass by the more generic representation —Si-$(L)_n$-$R^2$.

$R^2$ is any convenient hydrolyzable functional group that produces a hydroxyl function group (—OH) upon exposure to either acid or alkali hydrolysis conditions, i.e., $R^2$ is any convenient acid or alkali hydrolyzable group. In many embodiments, the acid or alkali hydrolyzable functional group is a group that yields a free carboxylic acid upon hydrolysis. In many of these embodiments, the hydrolyzable functional group is an ester.

As such, in many embodiments, the —Si-$(L)_n$-$R^2$ surface groups are esters of a carboxylic acid and a long chain alcohol (so that they include a carboxylic ester functional group), where the long chain alcohol is L and is covalently bound to the substrate surface via the Si linkage. Viewed another way, the —Si-$(L)_n$-$R^2$ surface groups are long chain esters that are hydrolyzable to yield a long chain alcohol that is bound to the substrate surface and free carboxylic acid, i.e., a surface bound hydroxyl group and a free carboxylic acid.

In many of the above embodiments, $R^2$ has the following formula: O—(CO)—$R^3$, where $R^3$ is, in many embodiments, an alkyl group as defined above. However, $R^3$ may be any group that does not unacceptably interfere with the acid hydrolysis of the functional group to produce a hydroxyl group, as described in greater detail below. Specific groups of interest include, but are not limited to: acetyl, alkyl, alkenyl, amino, benzyl, hydroxyl, halo, and the like. If $R^2$ has the formula O—(CO)—$R^3$ then (L)n will be terminated by a hydroxyl group after either acid or alkaline hydrolysis.

L represents a linker and n is 0 or 1, such that a linker may or may not be present. If a linker is present, it will generally be a $C_1$–$C_{24}$ hydrocarbylene linking group. Normally, L is $C_1$–$C_{24}$ alkylene, preferably $C_{10}$–$C_{18}$ alkylene.

The density of the $R^2$ hydrolyzable functional groups on the substrate surface, following reaction with the derivatizing composition, is determined by the relative proportions of the first and second silanes in the derivatizing composition. That is, a higher proportion of the second silane in the derivatizing composition will provide a greater density of $R^2$ groups, while a higher proportion of the first silane will give rise to a lower density of $R^2$ groups. Optimally, the first silane is present in the range of approximately 0 wt. % to 99.5 wt. % of the derivatization composition, preferably in the range of approximately 90 wt. % to 99 wt. % of the composition, while the second silane correspondingly is present in the range of approximately 0.5 wt. % to 100 wt. % of the derivatization composition, preferably in the range of approximately 1% wt. % to 10 wt. % of the composition.

In many embodiments, the resultant surface of the functionalized substrates contain both —Si—$R^1$ and Si-$(L)_n$-$R^2$ groups, present at a predetermined ratio, with the ratio determining both surface energy and density of functional groups. In other words, the functional surface of the substrate displays acid or alkali hydrolyzable functional groups. See also U.S. Pat. No. 6,258,454 for a further description of the general process of derivatizing a surface, the disclosure of which is herein incorporated by reference.

Conversion of Hydrolyzable Functional Groups to Hydroxyl Functional Groups

The next step in the subject methods is to convert the hydrolyzable functional groups on the substrate surface as described above to hydroxyl functional groups. The hydrolyzable functional groups are converted to hydroxyl functional groups using any convenient protocol. Both acid and alkali hydrolysis protocols find use in the subject invention.

In certain embodiments, acid hydrolysis is employed to convert the hydrolyzable groups to hydroxyl groups. In these embodiments, the substrate surface is subjected to acid hydrolysis conditions that convert the acid hydrolyzable functional groups to hydroxyl functional groups. To subject the substrate surface to acid hydrolysis conditions, the substrate surface is typically contacted with an acidic aqueous fluid under conditions and for a period of time sufficient to cause acid hydrolysis. Contact may be achieved using any convenient protocol, e.g., dispensing the acid solution onto the surface of the substrate, submersing the substrate in the aqueous fluid, flowing a volume of the aqueous fluid across the substrate surface, etc. Contact is carried out under appropriate conditions, e.g., at a temperature ranging from about room temperature to about 100° C., usually from about 40 to about 60° C., for a period of time ranging from about 10 minutes to about 6 hours, typically from about 1 hour to about 2 hours. By acid solution is meant a solution having a pH of less than about 7, typically about 1. The solution may include one or more different acids or derivatives thereof. Suitable acids that lack a hydrocarbon moiety, e.g., mineral acids, include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Also of interest are acids that include a hydrocarbon moiety, e.g., organic acids, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, methane sulfinic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms that may be neutralized by alkalies and replaced by organic radicals.

In other embodiments, hydrolysis of the hydrolyzable functional group is acheived by alkali hydrolysis, i.e., use of alkali hydrolysis conditions. To subject the substrate surface to alkali hydrolysis conditions, the substrate surface is typically contacted with an alkali fluid under conditions and for a period of time sufficient to cause alkali hydrolysis. Contact is carried out under appropriate conditions, e.g. at a temperature ranging from about room temperature to 100° C., usually from about room temperature to 50° C., usually from about 5 minutes to about 2 hours, typically from about 5 minutes to 30 minutes. By alkali solution is meant a solution having a pH greater than 7. The solution may include one or more different alkalis or derivatives thereof. Suitable alkalis include, for instance, sodium hydroxide, potassium hydroxide, etc., dissolved in water or the formation of the corresponding alkoxide by dissolution of the hydroxide in an alcohol such as methanol, ethanol etc. The alkali is dissolved in the solvent with a % wt of between 1 to 50%, preferably between 1 to 10%. The preferred solvent is an alcohol, either methanol or ethanol of any organic alcohol or mixture of one or more alcohols. Whereas it is well known that water based alkali solutions of, for instance, sodium hydroxide in water, destroy the siloxane surface (the point at which the silicon atom is attached to the substrate via an oxygen atom) quite easily(in less than an hour) this is not the case for alcohol based alkalis. Indeed the surface is stable to such solvents for long periods of time (at least greater than 3 days, if not more). As such, the alkali hydrolysis conditions employed are generally alcohol based alkali conditions.

The above hydrolysis protocols result in conversion of the hydrolyzable functional groups to hydroxyl groups. While the particular results achieved may vary, the percentage of initial hydrolyzable functional groups that are converted is, in many embodiments, at least about 5%, usually at least about 10% and more usually at least about 20 number % of the initial number of hydrolyzable functional groups, where the number % may be higher, e.g., 30, 40, 50, 60, 70, 80, 90, 95, 99. The resultant hydroxyl group functionalized surface may be used immediately for covalent ligand attachment or, where desired, further functionalized prior to ligand attachment. For example, in many embodiments the ligand to be covalently attached to the surface may be functionalized with a hydroxyl functional group, which provides for covalent attachment of the ligand to the substrate surface via reaction of the ligand functional group with the surface hydroxyl functional group.

Alternatively, the hydroxyl functional group may be converted to a number of different types of functional groups which are reactive to the ligand of interest, i.e., liand reactive functional groups. By ligand reactive functional groups is meant groups that react with moieties present on the target ligands, (i.e., the ligands to be deposited onto the surface and covalently bound thereto) in manner that produces a covalent bond or linkage between the ligand and the substrate surface. The hydroxyl functional groups may be converted to a variety of different types of reactive moieties using a variety of different protocols, depending on the particular nature of the ligand that is to be covalently bound to the substrate surface. Representative ligand reactive functional groups to which the initial hydroxyl functional groups may be converted include: aldehyes, amines, and the like. The particular ligand reactive functional group to which the initial hydroxyl group is converted will be chosen, at least in part, on considerations that include, but are not limited to: the nature of the ligand and functional groups that may be present thereon, ease of conversion, and the like.

The particular conversion protocol employed will vary with respect to the nature of the desired ligand reactive functional group, and may or may not involve the production of one or more intermediate groups. In one embodiment, the hydroxyl functional groups of the initial substrate surface are converted to aldehyde functional groups, e.g., via controlled oxidation to aldehyde functionalities, e.g., via Moffat oxidations, where primary alcohols are specifically and efficiently converted to the corresponding aldehydes under mild conditions. See e.g., Pftizner and Moffatt, Comp. Org Syn. 7, 291 (1991), J. Amer. Chem. Soc. (1965) 87:5670–78. In yet another embodiment, the surface hydroxyl groups are converted to amine reactive benzaldehyde functionalities using benzaldehyde phosphoramidites. More specifically, the hydroxyl moiety can be reacted with a benzaldehyde phosphoramidite, followed by acidic deprotection of the benzaldehyde moiety and basic deprotection of the phosphate moiety. Such protocols are known in the art, see e.g., WO 01/09385 and its priority application Ser. No. 09/364, 320, the disclosure of latter of which is herein incorporated by reference.

Following production of the hydroxyl functional groups, and any subsequent functionalization of the hydroxyl groups, as described above, the resultant hydroxyl functionalized surface can be employed in the fabrication of arrays, e.g., via polymeric ligand deposition where one or more polymeric ligands are contacted with the functionalized surface; or in situ polymeric ligand synthesis, as described immediately below in greater detail.

Polymeric Ligand Attachment

In many embodiments, the subject surfaces are employed in array fabrication where polymeric ligands are attached to the surface. In these embodiments, the ligands that are contacted with the substrate surface are typically polymeric binding agents. The polymeric binding agents may vary widely, where the only limitation is that the polymeric binding agents are made up of two more, usually a plurality of, monomeric units covalently attached in sequential order to one another such that the polymeric compound has a sequence of monomeric units. Typically, the polymeric binding agent includes at least 5 monomeric units, usually at least 10 monomeric units and more usually at least 15 monomeric units, where in many embodiments the number of monomeric units in the polymers may be as high as 5000 or higher, but generally will not exceed about 2000. In certain embodiments, the number of monomeric residues in the polymeric binding agent is at least about 50, usually at least about 100 and more usually at least about 150.

Polymeric binding agents of particular interest include biopolymeric molecules, such as polypeptides, nucleic acids, polysaccharides and the like, where polypeptides and nucleic acids, as well as synthetic mimetics thereof, are of particular interest in many embodiments.

In many embodiments, the polymeric binding agents are nucleic acids, including DNA, RNA, nucleic acids of one or more synthetic or non-naturally occurring nucleotides, and the like. The nucleic acids may be oligonucleotides, polynucleotides, including cDNAs, mRNAs, and the like. Where the polymeric compounds are nucleic acids, the nucleic acids will generally be at least about 5 nt, usually at least about 10 nt and more usually at least about 15 nt in length, where the nucleic acids may be as long as 5000 nt or longer, but generally will not exceed about 3000 nt in length and usually will not exceed about 2000 nt in length. In many embodiments, the nucleic acids are at least about 25 nt in length, usually at least about 50 nt in length and may be at least about 100 nt in length.

The polymers are characterized by having a functional moiety that reacts with the ligand reactive functional moiety present on the substrate surface to produce a covalent bond between the ligand and the substrate surface. The ligand may naturally include the desired reactive functionality, or may be modified to include the desired reaction functionality. Representative reactive functionalities of interest include, but are not limited to: amine groups, hydroxyl groups, sulfhydryl, phosphoramidite, anhydrides, and the like.

The polymers employed in the subject methods may be prepared using any convenient methodology. The particular means of preparing the polymer to include the requisite reactive group where it is not initially present will depend on the nature of the polymer and the nature of the reactive group that is to be incorporated into the polymer.

As mentioned above, in practicing the subject methods, typically at least two distinct polymers are contacted with the substrate surface that bears the reactive ligand functionalities. By distinct is meant that the two polymers differ from each other in terms of sequence of monomeric units. The number of different polymers that are contacted with the substrate surface may vary depending on the desired nature of the array to be produced, i.e. the desired density of polymeric structures. Generally, the number of distinct polymers that are contacted with the surface of the array will be at least about 5, usually at least about 10 and more usually at least about 100, where the number may be as high as 1,000,000 or higher, but in many embodiments will not exceed about 500,000 and in certain embodiments will not exceed about 100,000.

The polymers are generally contacted with the surface in an aqueous solvent, such that aqueous conditions are established at the surface location to which the polymer is to be covalently attached. The temperature during contact typically ranges from about 10 to 60 and usually from about 20 to 40° C. Following initial contact, the aqueous solution of polymer is typically maintained for a period of time sufficient for the desired amount of reaction to occur, where the period of time is typically at least about 20 sec, usually at least about 1 min and more usually at least about 10 min, where the period of time may be as great as 20 min or greater.

Each polymer is typically contacted with the substrate surface as part of an aqueous composition, i.e. an aqueous composition of the polymer in an aqueous solvent is contacted with the surface of the array. The aqueous solvent may be either water alone or water in combination with a co-solvent, e.g. an organic solvent, and the like. The aqueous composition may also contain one or more additional agents, including: acetic acid, monochloro acetic acid, dichloro acetic acid, trichloro acetic acid, acetonitrile, catalysts, e.g. lanthanide (III) trifluoromethylsulfate, lithium chloride, buffering agents, e.g. sodium phosphate, salts, metal cations, surfactants, enzymes, etc.

The aqueous polymer composition may be contacted with the surface using any convenient protocol. Generally, the aqueous polymer composition is contacted with the surface by depositing the aqueous polymer composition on the surface of the substrate. The aqueous volume may be deposited manually, e.g. via pipette, or through the use of an automated machine or device. A number of devices and protocols have been developed for depositing aqueous solutions onto precise locations of a support surface and may be employed in the present methods. Such devices include "pulse-jet" printing devices, mechanical deposition or pipetting devices and the like. See e.g. U.S. Pat. Nos. 4,877,745; 5,338,688; 5,474,796; 5,449,754; 5,658,802; 5,700,637; and 5,807,552; the disclosures of which are herein incorporated by reference. Robotic devices for precisely depositing aqueous volumes onto discrete locations of a support surface, i.e. arrayers, are also commercially available from a number of vendors, including: Genetic Microsystems; Cartesian Technologies; Beecher Instruments; Genomic Solutions; and BioRobotics.

The amount of fluid that is deposited may vary. For example, volumes ranging from about 1 nl to 1 pl, usually from about 60 to 100 nl may be deposited onto the substrate surface. Following contact and incubation for a period of time and under conditions sufficient for the desired reaction to occur, as described above, the surface of the resultant array may be further processed as desired in order to prepare the array for use, as described below. As such, the array surface may be washed to remove unbound reagent, e.g. unreacted polymer, and the like. Any convenient wash solution and protocol may be employed, e.g. flowing an aqueous wash solution, e.g. water, methanol, acetonitrile, and the like, across the surface of the array, etc. The surface may also be dried and stored for subsequent use, etc.

The above described protocols for array fabrication can be carried out using the devices described in U.S. Pat. Nos. 6,242,266; 6,232,072 and 6,180,351; the disclosures of which are herein incorporated by reference.

In Situ Synthesis

As indicated above, the substrate surfaces displaying hydroxyl functional groups can also be employed in situ ligand synthesis applications. The in situ synthesis methods include those described in U.S. Pat. No. 5,449,754 for synthesizing peptide arrays, as well as WO 98/41531 and the references cited therein for synthesizing polynucleotides (specifically, DNA) using phosphoramidite or other chemistry. Such in situ synthesis methods can be basically regarded as iterating the sequence of depositing: (a) a protected monomer onto predetermined locations on a substrate to link with either a suitably activated substrate surface (or with a previously deposited deprotected monomer); (b) deprotecting the deposited monomer so that it can now react with a subsequently deposited protected monomer; and (c) depositing another protected monomer for linking. Different monomers may be deposited at different regions on the substrate during any one cycle so that the different regions of the completed array will carry the different biopolymer sequences as desired in the completed array. One or more intermediate further steps may be required in each iteration, such as oxidation and washing steps. The substrate surfaces may also be employed in the well known light directed in situ polymeric array synthesis protocols, including those described in U.S. Pat. No. 6,329,143.

The above protocol produces ligand arrays that can be employed in a variety of different applications, as described in greater detail below.

Arrays

Also provided by the subject invention are arrays of polymeric binding agents produced according to the subject methods, as described above. The subject arrays include at least two distinct polymers that differ by monomeric sequence immobilized on e.g., covalently to, different and known locations on the substrate surface. In certain embodiments, each distinct polymeric sequence of the array is typically present as a composition of multiple copies of the polymer on the substrate surface, e.g. as a spot on the surface of the substrate. The number of distinct polymeric sequences, and hence spots or similar structures, present on the array may vary, but is generally at least 2, usually at least 5 and more usually at least 10, where the number of different spots on the array may be as a high as 50, 100, 500, 1000, 10,000 or higher, depending on the intended use of the array. The spots of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm$^2$, where the density may be as high as $10^6$ or higher, but will generally not exceed about $10^5$ spots/cm$^2$. In other embodiments, the polymeric sequences are not arranged in the form of distinct spots, but may be positioned on the surface such that there is substantially no space separating one polymer sequence/feature from another.

In the broadest sense, the arrays of the subject invention are arrays of polymeric binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini, e.g. the 3' or 5' terminus. In other embodiments, the arrays are arrays of polypeptides, e.g., proteins or fragments thereof.

Utility

The subject arrays find use in a variety of different applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest is contacted with an array produced according to the subject methods under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g. through use of a signal production system, e.g. an isotopic or fluorescent label present on the analyte, etc. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in: U.S. Pat. Nos. 4,591,570; 5,171,695; 5,436,170; 5,486,452; 5,532,128; and 6,197,599; the disclosures of which are herein incorporated by reference; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

In certain embodiments, the subject methods include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

As such, in using an array made by the method of the present invention, the array will typically be exposed to a sample (for example, a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER scanner available from Agilent Technologies, Palo Alto, Calif. Other suitable apparatus and methods are described in U.S. patent applications: Ser. No. 09/846,125 "Reading Multi-Featured Arrays" by Dorsel et al.; and Ser. No. 09/430,214 "Interrogating Multi-Featured Arrays" by Dorsel et al. As previously mentioned, these references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

Kits

Finally, kits for use in analyte detection assays are provided. The subject kits at least include the arrays of the subject invention. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the subject array assay devices for carrying out an array based assay. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, The following examples are offered by way of illustration and not by way of limitation.

EXPERIMENTAL

I. Representative Protocol for Preparation Acetate Substrates:
1) To one liter of toluene is added 0.25 mls of water. The mix is allowed to stir overnight or until all the water has been dissolved.
2) 4 mls of decyltrichlorosilane, $CH_3(CH_2)_9Si(Cl)_3$, and 0.4 mls of 11-trichlorosilylundecyl acetate, $CH_3(CO)O(CH_2)_{11}Si(Cl)_3$ are added to 250 mls of the above toluene containing either glass or silica surfaces that are to be derivatized.
3) The above solution is stirred at room temperature for 2 hours, after which the surfaces are removed from solution and rinsed in toluene, methanol and finally water. They are then dried in a stream of dry nitrogen.
4) The above surfaces are then hydrolyzed using either acid or alkaline conditions:

A. Acid Hydrolysis:

The surfaces are added to a vessel containing a solution of either hydrochloric acid or sulfuric acid in water, typically about 10% by weight. The solution is then stirred at 50° C. for two hours. The surfaces are then rinsed with water and air-dried in a stream of dry nitrogen.

B. Alkali Hydrolysis:

The surfaces are added to a vessel containing a solution of sodium hydroxide in denatured ethanol, typically 0.1 normal in concentration and stirred for 10 minutes at room temperature. After hydrolysis the surfaces are rinsed in water and air-dried in a stream of dry nitrogen.

II. Surface Characterization
1) Surfaces were monitored for the disappearance of the IR (infrared) signal of the acetate group at 1740 $cm^{-1}$ during both acid and alkali hydrolysis.
2) Dyes (CY3 and CY5) were attached to the formed hydroxyl group and the resulting absorbance of the attached dye was measured. These dyes do not attach to acetate groups which are present prior to hydrolysis.
3) A 100% acetate surface was constructed and hydrolyzed to a hydroxyl surface. The contact angle for this surface was determined to be about 60 degrees. A decyltrichlorosilane was then attached to this hydroxyl surface. The contact angle went up to 100 degrees. This finding shows that the hydrophilic hydroxyl surface had been replaced by the hydrophobic decyl surface.

Results from the above studies indicated the presence of a hydroxyl functionalized surface.

III. Arrays

The above hydroxyl functionalized surfaces were employed to prepare oligonucleotide microarrays by depositing oligonucleotide probes on the hydroxyl functionalized surface. The resultant arrays were observed to be functional.

It is evident from the above results and discussion that an important new protocol for preparing polymeric arrays, particularly nucleic acid arrays, is provided by the subject invention. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing an array of at least two different ligands covalently bonded to a surface of a substrate, said method comprising:
   (a) providing a silica comprising substrate having a surface displaying carboxylic ester functional groups that produce surface bound hydroxyl functional groups and a free carboxylic acid upon hydrolysis, wherein said carboxylic ester functional groups are moieties of silane molecules covalently bonded to said surface;
   (b) converting said carboxylic ester functional groups to produce a free carboxylic acid and a substrate having a surface displaying hydroxyl functional groups; and
   (c) producing at least two different ligands covalently bound to said surface to produce said array by either;
      contacting said surface with said at least two different ligands; or
      in situ synthesizing said ligands on said surface.

2. The method according to claim 1, wherein said covalently bound ligands are produced on said surface by contacting said surface with said at least two different ligands.

3. The method according to claim 1, wherein said covalently bound ligands are produced on said surface by in situ synthesis of said ligands on said surface.

4. The method according to claim 1, wherein said substrate is glass.

5. The method according to claim 1, wherein said converting step (b) comprises subjecting said surface to acid hydrolysis conditions.

6. The method according to claim 1, wherein said converting step (b) comprises subjecting said surface to alkali hydrolysis conditions.

7. The method according to claim 1, wherein said ligands are polymers.

8. The method according to claim 7, wherein said polymers are nucleic acids.

9. The method according to claim 7, wherein said polymers are peptides.

10. A method of producing an array of at least two different polymer ligands covalently attached to a surface of a substrate, said method comprising:
 (a) providing a silica comprising substrate having a surface modified with silane molecules having carboxylic ester functional groups that produce surface bound hydroxyl functional groups and a free carboxylic acid upon hydrolysis, wherein said carboxylic ester functional groups are moieties of silane molecules covalently bonded to said surface;
 (b) converting said carboxylic ester functional groups to produce a free carboxylic acid and a substrate having a surface displaying hydroxyl functional groups; and
 (c) contacting said surface of said substrate displaying hydroxyl functional groups with said at least two different polymer ligands to covalently bond said at least two different polymer ligands to said surface and produce said array.

11. The method according to claim 10, wherein said substrate is glass.

12. The method according to claim 10, wherein said converting step (b) comprises subjecting said surface to acid hydrolysis conditions.

13. The method according to claim 10, wherein said converting step (b) comprises subjecting said surface to alkali hydrolysis conditions.

14. The method according to claim 10, wherein said polymer ligands are nucleic acids.

15. The method according to claim 10, wherein said polymer ligands are peptides.

16. A method of producing an array of at least two different nucleic acids covalently attached to a surface of a substrate, said method comprising:
 (a) providing a silica comprising substrate having a surface displaying carboxylic ester functional groups that produce surface bound hydroxyl functional groups upon acid hydrolysis, wherein said carboxylic ester functional groups are moieties of silane molecules covalently bonded to said surface;
 (b) converting said carboxylic ester functional groups to hydroxyl functional groups to produce a free carboxylic acid and a surface displaying hydroxyl functional groups; and
 (c) depositing each of said least two different nucleic acids onto different regions of said surface to covalently bond said at least two different nucleic acids to said surface and produce said array.

17. The method according to claim 16, wherein said nucleic acids are oligonucleotides.

18. The method according to claim 16, wherein said nucleic acids are polynucleotides.

19. The method according to claim 18, wherein said polynucleotides are cDNAs.

20. A method of producing a surface modified substrate, said method comprising:
 (a) providing a silica comprising substrate having a surface displaying carboxylic ester functional groups that produce surface bound hydroxyl functional groups and a free carboxylic acid upon acid hydrolysis, wherein said carboxylic ester functional groups are moieties of silane molecules covalently bonded to said surface;
 (b) converting said carboxylic ester functional groups to surface bound hydroxyl functional groups.

21. The method according to claim 20, wherein said substrate is glass.

22. The method according to claim 20, wherein said converting step (b) comprises subjecting said surface to acid hydrolysis conditions.

23. The method according to claim 20, wherein said converting step (b) comprises subjecting said surface to alkali hydrolysis conditions.

* * * * *